US008426155B2

(12) United States Patent
Hartmer et al.

(10) Patent No.: US 8,426,155 B2
(45) Date of Patent: Apr. 23, 2013

(54) PROTEOME ANALYSIS IN MASS SPECTROMETERS CONTAINING RF ION TRAPS

(75) Inventors: Ralf Hartmer, Hamburg (DE); Jochen Franzen, Bremen (DE)

(73) Assignee: Bruker Daltonik, GmbH, Bremen (DE)

( * ) Notice: Subject to any disclaimer, the term of this patent is extended or adjusted under 35 U.S.C. 154(b) by 0 days.

(21) Appl. No.: 13/311,022

(22) Filed: Dec. 5, 2011

(65) Prior Publication Data

US 2012/0156707 A1 Jun. 21, 2012

(30) Foreign Application Priority Data

Dec. 15, 2010 (DE) ......................... 10 2010 054 580

(51) Int. Cl.
*C12Q 1/37* (2006.01)

(52) U.S. Cl.
USPC ........................................................... 435/23

(58) Field of Classification Search .................... 435/23; 250/282
See application file for complete search history.

(56) References Cited

U.S. PATENT DOCUMENTS 5,770,860 A * 6/1998 Franzen ........................ 250/288
5,952,653 A 9/1999 Covey
7,582,862 B2 * 9/2009 Hartmer ........................ 250/282
7,737,398 B2 * 6/2010 Michelmann ................. 250/292
2003/0124606 A1 7/2003 Suckau
2004/0245452 A1 12/2004 Bateman
2007/0084998 A1 * 4/2007 Franzen et al. ............... 250/287
2008/0093546 A1 4/2008 Hartmer
2008/0156980 A1 * 7/2008 Rather et al. .................. 250/287

FOREIGN PATENT DOCUMENTS

GB 2387653 A * 10/2003

OTHER PUBLICATIONS

Venable J. et al. Automated Approach for Quantitiative Analysis of Complex Peptide Mixtures from Tandem Mass Spectra. Nature Methods 1(1)1-7, Oct. 2004.*
Panchaud, A., Scherl, A., Schaffer, S.A. Von Haller, V.D., Kulasekara, S.D., Miller, S.I. and Goodlet, D.R. "Precursor Acquisition Independent from Ion Count: How to Dive Deeper into the Proteomics Ocean", Analytical Chemistry, v. 81, n. 15, pp. 6481-6487 (Aug. 2009).

* cited by examiner

*Primary Examiner* — Ralph Gitomer
(74) *Attorney, Agent, or Firm* — ROBIC, LLP

(57) ABSTRACT

A complex protein mixture is analyzed by jointly digesting the mixture, separating the digest peptides chromatographically or electrophoretically, and ionizing the digest peptides eluting from the separation device by an ionizing method that generates multiply charged ions. Digest peptide ions within a pre-selected range of m/z-values are isolated in an RF ion trap and subsequently reduced in their charge state. The charge-reduced ions can be measured with very high sensitivity. By repeating this process with adjacent isolation mass windows within the time duration of each separation peak, it is possible to determine the masses m, the prevalent charge states z, the retention times t, and the intensities i of a huge number of digest peptides of the complex protein mixture in a single separation run.

20 Claims, 5 Drawing Sheets

PROTEOME ANALYSIS IN MASS SPECTROMETERS CONTAINING RF ION TRAPS

This application claims benefit of priority to application German 10 2010 054 580.5 filed Dec. 15, 2010.

BACKGROUND

This invention relates to the analysis of complex protein mixtures, such as whole proteomes, by joint enzymatic digestion, followed by chromatographic or electrophoretic separation and mass spectrometric analysis of the digest peptides. A proteome is defined as the community of all the proteins of a species (e.g. human proteome; mouse proteome), of an organ (brain, liver, blood plasma proteome), of a type of cell (cell proteome) or even a type of organelle (organelle proteome). Since there are hundreds of cell types in a higher organism (about 230 human cell types), there are also hundreds of cell proteomes. There are proteins which are common to all cells of the organism (housekeeping proteins), and those which are specific to one cell type. Moreover, a proteome is not constant in its composition; it changes qualitatively and quantitatively with age, state of health or stress of an organism, e.g. stress brought about by the administration of medication or stress caused by a tumor. Unusual over-expressions and under-expressions of certain proteins can provide information on the stress.

Naturally, hitherto unknown proteins of a proteome are of special interest. In the area of pharmacology, for instance, they are of interest both for their use as pharmaceutical target proteins (targets) and also as active substances, which may be used as pharmaceutical products. Examples of proteins used as pharmaceutical products are insulin and estrogen; there are hundreds of other examples. The proteins, which are active substances like enzymes, are mainly present only in very low concentrations and often escape the classical method of proteome analysis. By those proteins whose quantity changes by over-expression or under-expression due to stress on the cell community, valuable information is provided about the functioning of the cells.

Mammals are estimated to have by far more than 100,000 proteins, whose basic blueprints can be found in around 10,000 to 30,000 genes (at present knowledge, the human genome comprises 20,300 genes). There are estimates that so-called "alternative splicing" can produce, on the statistical average, around three and a half different types of proteins from one single gene; in addition to this, many more proteins result from post-translational modifications (PTM) like shortening or lengthening the protein, methylations, phosphorylations, glycosylations, formation of lipoproteins and many others. A cell proteome may contain a few thousand to a few ten thousand proteins. At present, there are estimates that not even half of the human proteins are known.

In order to jointly analyze as many proteins of complete proteomes as possible there are essentially two different approaches: "top-down" or "bottom-up". In the top-down method, the proteins are first chromatographically or electrophoretically separated and only then fragmented (for example by enzymatic digestion, or by types of fragmentation commonly used in mass spectrometers, such as collision-induced fragmentation or multi-photon absorption) in order to analyze the fragment peptides mass spectrometrically. If the fragment peptides belonging to a protein are known in advance; an accurate mass determination of the fragment peptides is then usually sufficient to identify the protein with the aid of databases. In the bottom-up method, in contrast, a mixture containing all the proteins is enzymatically digested jointly; a daughter ion spectrum of each digest peptide must then be measured in order to identify every single digest peptide by recognition of parts of its amino acid sequence and to assign it to a protein. In this method, the digest peptides are usually separated by liquid chromatography. The term "daughter ion mass spectrum" means a mass spectrum of the fragment ions of a selected ion species; the ions of an ion species selected for the fragmentation are usually called "parent ions".

A frequently used top-down analytical method for the proteins of a proteome is essentially based on the separation of the dissolved proteins by 2D-gel electrophoresis, staining the proteins, punching out little gel pieces with stained proteins, de-staining, enzymatic digestion within the piece of gel, and subsequent MALDI mass spectrometric investigation of the digest peptides in time-of-flight mass spectrometers, whereby precise masses of the digest peptides as well as daughter ion spectra of the digest peptides can be obtained. If the proteins are present in protein sequence databases, they can be found via the precise masses of the digest peptides. If the identification is ambiguous, daughter ion spectra of individual digest peptides can be used for confirmations. If the protein is not present in the protein sequence database, it is possible to search in EST databases (Expressed Sequence Tags) which have been obtained from RNA, in cDNA data or in "open reading frames" of the DNA data of the genome.

This method has the advantage that the protein to which a digest peptide belongs is known in advance, at least if the separation by 2D-gel electrophoresis was sufficiently good. As a rule, only 10 to around 70 percent of the sequence of a protein, in most cases below 50 percent, is covered by digest peptides. This is called "coverage". If the protein is present in the database, an identification often only requires knowledge of the precise masses of several digest peptides, as has been stated before; if the results are ambiguous, which frequently occurs when the mass determination is not accurate enough, an additional daughter ion spectrum of a peptide, which reflects at least parts of its amino acid sequence, leads to a certain identification.

In the 2D-gel it is quite common that several thousand spots are stained and found, although it usually turns out during the analyses that only a few hundred different proteins are analytically found in one proteome with this method. However, a proteome is expected to comprise many times this number of proteins.

An analytical bottom-up method basically performs the analysis of mixtures of proteins by the joint digestion of all the proteins of this mixture, liquid chromatographic (LC) separation of the digest peptides, electrospray ionization (ESI) and automatic methods for the acquisition of daughter ion spectra to determine at least parts of the amino acid sequence of the digest peptides in tandem mass spectrometers (MS/MS). When this joint digestion of the proteins and liquid chromatographic separation method is used, information concerning the protein to which a peptide belongs is no longer provided by the analytical method per se. In this case the protein to which different digest peptides belong can only be determined with the aid of daughter ion spectra and searches in databases. Excellent computer programs have been developed for searching the databases and for collating the peptides which form a protein.

This method of real time LC/MS/MS analysis is performed, for example, in RF ion trap mass spectrometers or in time-of-flight spectrometers with orthogonal ion injection and prior separation and fragmentation in upstream quadrupole filters (Q-OTOF). These instruments have a total acquisition time for a primary mass spectrum and subsequent daughter ion spectra of around half a second or even less. In a high-resolution liquid chromatogram, a maximum of about twenty to thirty different daughter ion spectra can be acquired within a chromatographic peak of around ten seconds width at half height. In a chromatography run of three hours, this means a maximum of 20,000 to 30,000 daughter ion spectra, if in fact so many digest peptides are detected in the primary mass spectra. Usually, however, this is not the case. For one proteome, usually only a few thousand digest peptides are found above the detection limit in the primary spectra. This means that around 500 to 1,000 proteins can be identified, in best cases around 1,500 proteins using mass spectrometers of highest sensitivity. At present, this seems to be a kind of magic limit, in spite of the fact that a proteome should show many times this number of proteins.

A different bottom-up method for the mass spectrometric analysis of a complex protein mixture is described in DE 101 58 860 B4 (D. Suckau et al., 2001). It comprises the following steps: a) joint enzymatic digestion of all the proteins in the protein mixture, b) liquid chromatographic separation of the digest peptides in the mixture, c) capture of several hundred fractions of the chromatographic eluent, each on a sample site of a sample support which is coated in advance with matrix substance, d) acquisition of mass spectra and daughter ion mass spectra with ionization by matrix-assisted laser desorption (MALDI) in suitable time-of-flight mass spectrometers, and e) identification of the associated proteins by searching in protein sequence, EST, cDNA or DNA databases. This method has the advantage of acquiring as many daughter ion spectra as there are peptides in a sample up to the complete consumption of the sample, and can find around five times more proteins than the 2D-gel electrophoresis method, but still is also limited to about 500 to 1,500 proteins.

The publication "Precursor Acquisition Independent from Ion Count: How to Dive Deeper into the Proteomics Ocean" by A. Panchaud et al., Anal. Chem. 2009, 81, 6481-6488 has elucidated a further bottom-up method which was carried out in RF ion trap mass spectrometers and which makes it possible to find far more digest peptides than with any previous method. The authors gave the method the acronym "PACIFIC" (Precursor Acquisition Independent From Ion Count).

The method is based on the long-recognized observation that, with RF ion trap mass spectrometers, the detection limits for daughter ions are significantly lower than those for the measurement of the unfragmented primary ions. If, in a primary spectrum, no signal is detected above the background noise at one mass, but an ion species is assumed to be present at that mass, it is possible to fill the ion trap to a very high level with ions, then remove all ions apart from the ones that are assumed to be there, fragment the assumed ions and acquire the daughter ion spectrum of the assumed ions. It can be shown that the detection limits for daughter ion spectra acquired in such a way are up to a factor of a hundred lower than those of the primary spectra. This observation can be used to search "blindly" for peptide ions which are far below the detection limit.

The method of A. Panchaud et al. thus blindly isolates mass ranges each measuring around 2.5 dalton, fragments the ions by collisions with residual gas molecules and measures the daughter ion spectrum. Cyclic repetition of eleven of these daughter ion measurements covers a mass range of 13.5 dalton, with overlaps which were inserted as a precaution, and takes around three seconds; the whole HPLC run is now scanned with this repeat cycle; several cycles are passed through for each HPLC peak of around 10 seconds full width at half-maximum. In consecutive HPLC runs, further new mass ranges, each of 13.5 mass units, are now scanned so that, after 67 HPLC runs, each of three hours duration, daughter ion mass spectra within the mass range from 400 to 1,400 dalton are obtained. This method was used for bacteria to determine far more than 2,000 of the proteins from around 50,000 measured digest peptides in 4.2 days. For human plasma, more than twice the number of proteins was determined than with methods used up to now.

As advantageous as this method may be with respect to the detectability of proteins, the time of several days required is a disadvantage for routine applications.

In the article "Automated approach for quantitative analysis of complex peptide mixtures from tandem mass spectra" by J. D. Venable et al. (Nature Methods, Vol. 1, No. 1, 2004), a similar method is described, but a broader width of 10 to 15 dalton is used for the isolation window, the ions are fragmented, and the daughter ions of peptides of a mixture of two proteomes with isotopically marked proteins are compared quantitatively.

The methods described are carried out in mass spectrometers containing RF ion traps and are based essentially on the special characteristics of these RF ion traps. In principle, both two-dimensional (linear) and three-dimensional ion traps can be used. As those skilled in the art are aware, the ions are kept in these ion traps by so-called pseudopotentials, and the effect of the pseudopotentials on the ions is inversely proportional to their mass-to-charge ratio m/z. No ions can be stored in the ion trap below a cut-off mass, which can be set via the RF voltage. In the ion trap, the lightest ions above the cut-off mass $(m/z)_{lim}$ collect in the center, the heavier ones are further toward the outside, the heavier they are, because the space charge drives the heavier ions further out against the pseudopotential, which has a weaker effect on them. This type of ion trap can be filled with around $10^7$ to $10^8$ ions in total; further filling causes heavier ions to be increasingly lost and lighter ions to be enriched. A mass spectrum cannot be acquired with an RF ion trap filled with such high numbers of ions, however, because the space charge hinders the mechanism that ejects separate ions. Modern RF ion trap mass spectrometers can provide a qualitatively good mass spectrum with only around 10,000 to 50,000 ions at maximum, but then with a resolution which even makes it possible to clearly recognize the isotopic pattern of quadruply or even quintuply charged ions. Mass spectrometers of this type with mass ranges up to m/z=3,000 dalton are commercially available.

To acquire qualitatively good daughter ion spectra of selected parent ions, it is advantageous to initially fill the ion trap with so many parent ions that, after their isolation and fragmentation, sufficient daughter ions still remain for a good daughter ion spectrum. This can often only be achieved by first greatly overfilling the ion trap with ions, for instance, with $10^6$ or even $10^7$ ions, depending on the concentration of the parent ions in the mixture of ions, and then specifically ejecting the ions not desired. This process is known as "isolation of the parent ions", and the manufacturers of RF ion trap mass spectrometers provide appropriate methods for it, which can be carried out by the control software of the mass spectrometers. Usually it is not only the monoisotopic ions of the parent ions, but all the ions of an isotopic group which are isolated. After the isolation, the parent ions are fragmented to daughter ions; these are measured as a mass spectrum. As described above, this acquisition method for daughter ion spectra can be used not only for ions which become visible in the primary mass spectrum, but also "blindly" or "non-selectively" for those ions which do not stand out from the background, but are only assumed to be present. The background in HPLC-coupled ion traps originates from many sources:

ions from solvent complexes, from impurities of the solvents, from "column bleed", from impurities from the ion source or the inlet capillary, and from impurities from the mass spectrometer, which are ionized via a protonation by injected ions. These ions are usually singly charged; multiply charged ions are the exception here.

In view of the above a need exists to provide a method whereby the presence and/or the identity of digest peptides of an enzymatically digested complex mixture of proteins can be determined with detection limits which are much lower than those of presently known methods.

SUMMARY

In accordance with the principles of the present invention, digest peptides are identified by enzymatically digesting the proteins of a complex protein mixture, separating the peptides of the digest with a liquid chromatograph (HPLC) or another separation device, ionizing the peptides eluting at a given retention time t from the separation device with an ionization method which, like electrospraying (ESI), generates multiply charged ions. However, in contrast to conventional method, the method of the invention subjects the ions to a special mass spectrometric analytical method with very low detection limits in a mass spectrometer with an RF ion trap.

By this special mass spectrometric analytical method, the RF ion trap will be initially greatly overfilled, and the ions with charge-related masses m/z within an isolation mass window with a lower limit $(m/z)_b$ and a broad width of $\Delta(m/z)$ will be isolated by the ejection of all other ions, the aim still being to have a greatly overfilled ion trap. Alternatively, it is also possible to fill the isolation mass window with ions already isolated by means of an upstream mass filter. Both two-dimensional and three-dimensional RF ion traps may be used. The width of the isolation window should amount to at least 20 dalton, but preferably much wider. The number z of charges of the multiply charged ions, usually up to z=5, in this isolation mass window is now reduced by reactions with reactant ions, for example by proton transfer reactions (PTR), and thus the m/z-values of the charge-reduced ions are shifted out of the isolation mass window. The reactant ions for the charge stripping must have a charge of opposite polarity to that of the digest peptide ions; negative reactant ions are used for the charge reduction of positively charged digest peptide ions, and positive reactant ions for the charge reduction of negative digest peptide ions. The ions with m/z-values remaining in the isolation mass window between $(m/z)_b$ and $((m/z)_b+\Delta(m/z))$ are predominantly singly charged ions of impurities, not having reacted at all. If the mass spectrum of the charge-reduced ions is to be measured with the RF ion trap itself, the ions having remained in the isolation mass window are now removed by ejection. This reduces the filling level of the ion trap considerably, which is necessary to obtain a mass scan of good quality. The charge-reduced ions with m/z-values outside this isolation mass window can now be measured as a well-resolved mass spectrum, showing very high sensitivity for the digest peptide ions. From these mass spectra, it is possible to determine the masses m, the charge states z, the retention times t and the intensities i of the digest peptide ions before their charge reduction.

The maximum width of the isolation mass window is determined by the fact that the masses m/z of the multiply charged ions should lie, after charge reduction, outside the isolation mass window.

Thus the method for the mass spectrometric analysis of a complex protein mixture in mass spectrometers with an RF ion trap comprises the steps:

jointly digesting the proteins of the protein mixture, separating the digest peptides by a separation method like HPLC or capillary electrophoresis, ionizing the peptides of the digested protein mixture with an ionization method which produces multiply charged ions, filling the RF ion trap with digest peptide ions having charge-related masses m/z between $(m/z)_b$ and $((m/z)_b+\Delta(m/z))$, reducing the number z of charges of the peptide ions by introducing reactant ions into the RF ion trap, and acquiring a mass spectrum of the charge-reduced ions.

This method for the acquisition of a mass spectrum of charge-reduced digest peptide ions with original charge-related masses in the chosen m/z-window only takes around 300 to 500 milliseconds. The method makes it possible to acquire spectra with around six to twelve different isolation mass windows $\Delta(m/z)$ in quick succession in around only two to six seconds; the isolation mass windows can be chosen so that they cover the complete mass range of interest with minor overlapping by a few daltons. Since acquisition methods with the consecutive isolation mass windows can be run through several times within the time course of an HPLC peak of around 10 to 15 seconds full width at half-maximum, it is possible to determine the masses m, the original charge states z before the charge reduction, the retention times t and the intensities i of many of the digest peptides of a complex proteome in a single HPLC run with high dynamic range of measurement, the overwhelming majority of these digest peptides having concentrations far below the detection limits of mass spectra of the primary ions. Most of the digest peptides discovered here cannot be detected with conventional methods, which involve initially determining the digest peptides above the detection limit using mass spectra of the primary ions, and then acquiring daughter ion spectra from these.

These data m, z, t and i of the digest peptides can already provide information on the under-expression or over-expression of proteins when compared with the same measurements on reference proteomes. If desired, this knowledge of the data on the digest peptides can also be used to specifically acquire daughter ion spectra of all the digest peptides in only a few subsequent HPLC runs, because it is quite possible to measure up to 40,000 daughter ion spectra in a three-hour HPLC run. This method finds many times the number of proteins than methods used hitherto have been able to find.

If additionally a mass spectrum of the primary digest peptides is also acquired in every cycle, this will find the highly abundant digest peptide ions. The dynamic range of measurement can be extended with this data by using resonant excitation to specifically eject the outstandingly abundant digest peptide ions during the filling and isolation processes. This shifts the measuring range for the remaining digest peptide ions to lower concentrations.

In the method described above, the mass spectrum of the charge-reduced ions was measured in the radio frequency ion trap of the mass spectrometer itself. However, this type of spectral acquisition has limited mass resolution and limited mass accuracy. It can therefore be advantageous to transfer the charge-reduced ions from the RF ion trap into another ion analyzer of higher mass resolution and mass accuracy, and to acquire the mass spectrum of the charge-reduced ions there. Time-of-flight mass spectrometers with orthogonal ion injection (OTOF), ion cyclotron resonance mass spectrometers (ICR-MS) or electrostatic Kingdon trap mass spectrometers are particularly suitable for this purpose.

DETAILED DESCRIPTION

By applying the principles of the invention it is possible to analyze an extremely complex mixture of several ten thousand digest peptides with very high sensitivity, low detection limits and high dynamic range of measurement. The mixture is obtained by the enzymatic digestion of a mixture of thousands of proteins which is already complex per se, for example from a proteome of a tissue with the same type of cells, or from the proteome of a colony of bacteria.

As in most conventional bottom-up methods, the digest peptides are preferably separated by liquid chromatography (HPLC), or alternatively by other separation methods such as capillary electrophoresis. The eluting peptides are preferably ionized by electrospray ionization (ESI) which predominantly generates multiply charged ions; in the case of tryptic digest peptides, these are predominantly doubly to quadruply charged ions, with some quintuply charged ions of larger peptides. But any other ionization method which generates multiply charged ions can also be used instead of electrospray ionization. According to the invention, the predominantly multiply charged ions are now subjected to a special mass spectrometric analysis in a mass spectrometer containing an RF ion trap. A simple mass spectrometer which can be used for this purpose is shown with some details in FIG. 1; other types of mass spectrometers are presented more schematically in FIGS. 6 to 9.

The special mass spectrometric analysis method of the invention aims to detect a majority of the digest peptides within a relatively broad range of mass to charge ratios m/z which jointly elute from a separation device at a given time t, in a single mass spectrum using a spectrum acquisition method which only takes around 300 to 500 milliseconds.

With this method, the ion trap is initially overfilled as much as possible with ions, and the ions inside an isolation mass window with a lowest mass $(m/z)_b$ and a width of $\Delta(m/z)$ are isolated by ejection of all other ions, the aim being to still have a large overfill of the ion trap. The term "overfill" relates here to the optimum filling of a maximum of around 50,000 ions, which is necessary in order to acquire a qualitatively good mass spectrum with the RF ion trap itself. The overfilling of the ion trap can quite easily amount to $10^6$ to $10^7$ ions. It assists the filling if the RF voltage is set so that the lower limit $(m/z)_b$ of the isolation mass window begins with the lower cut-off mass $(m/z)_{lim}$ for any ion storage, because at high overfill, the light ions which are to be collected in the isolation mass window are then automatically enriched due to the increasing loss of the heavier ions. The isolation then consists in the ejection of all ions above the selected isolation mass window.

Figure 1:
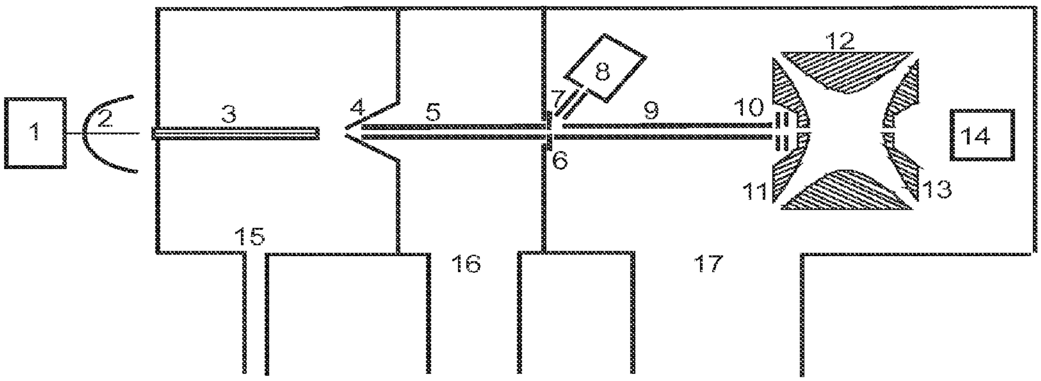
FIG. 1 (Prior Art)
FIG. 1 is a schematic representation of an ion trap mass spectrometer to carry out the methods according to this invention, with a chromatographic or electrophoretic separation device (1), an electrospray ion source (2), an electron attachment ion source (8) for the generation of negative ions and a 3D RF ion trap with two end cap electrodes (11, 13) and one ring electrode (12). The ion guide (9), which preferably takes the form of an octopole rod system, can guide both positive and negative ions to the ion trap. Different types of reactant ions from the ion source (8) can be used for proton reduction by PTR, or for a fragmentation of the digest peptide ions by electron transfer dissociation (ETD). Mass spectrometers of this type are commercially available.
Figure 2:
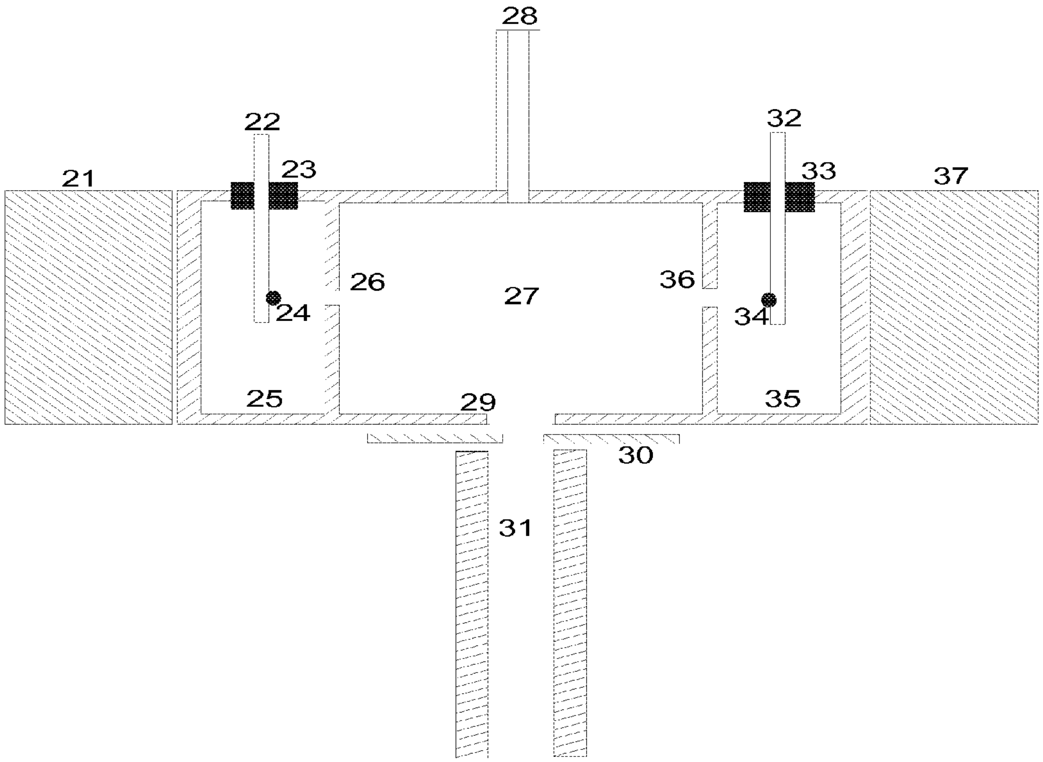
FIG. 2 shows an electron attachment ion source in which an electron beam, originating from the thermionic cathode (24) and guided by two magnets (21) and (37), negatively ionizes gaseous substances in the chamber (27) in the presence of methane or other cooling gases. These substances enter through the inlet (28) together with the methane. The anions which are generated are extracted from the opening (29) with the aid of the extraction diaphragm (30) and introduced into the hexapole ion guide (31). With a low extraction voltage practically only radical anions are extracted, suitable for electron transfer dissociation (ETD), while at higher extraction voltage predominantly only non-radical anions for proton transfer reactions (PTR) are extracted. Mass spectrometers with ion sources of this type are commercially available.

The charge state z of the predominantly multiply-charged digest peptide ions, which are now stored in the ion trap in addition to a sometimes overwhelming number of background ions, is now reduced by the introduction of reactant ions. With lower values of z the m/z-values of the charge-reduced ions now appear in a higher region of the mass-to-charge ratios m/z. The reactant ions can be generated in an electron attachment ion source, for example, as depicted in FIG. 2. In FIG. 1, an electron attachment ion source (8) is installed in an RF ion trap mass spectrometer. The reactions for the charge reduction, which are described in U.S. Pat. No. 7,582,862 B2 (R. Hartmer, 2006), produce singly, doubly and triply charged ions which have originated from quadruply charged ions by charge reduction, at a mass-to-charge ratio m/z which is greater by the factors 4.0, 2.0 and 1.333 respectively. From triply charged ions, doubly charged ones appear which are "heavier" by a factor of 1.50, singly charged ones by a factor of 3.0. Singly charged ions which originate from doubly charged ions are "heavier" by a factor of 2.0. From quintuply charged ions, quadruply, triply, doubly and singly charged ions are generated.

Figure 3:
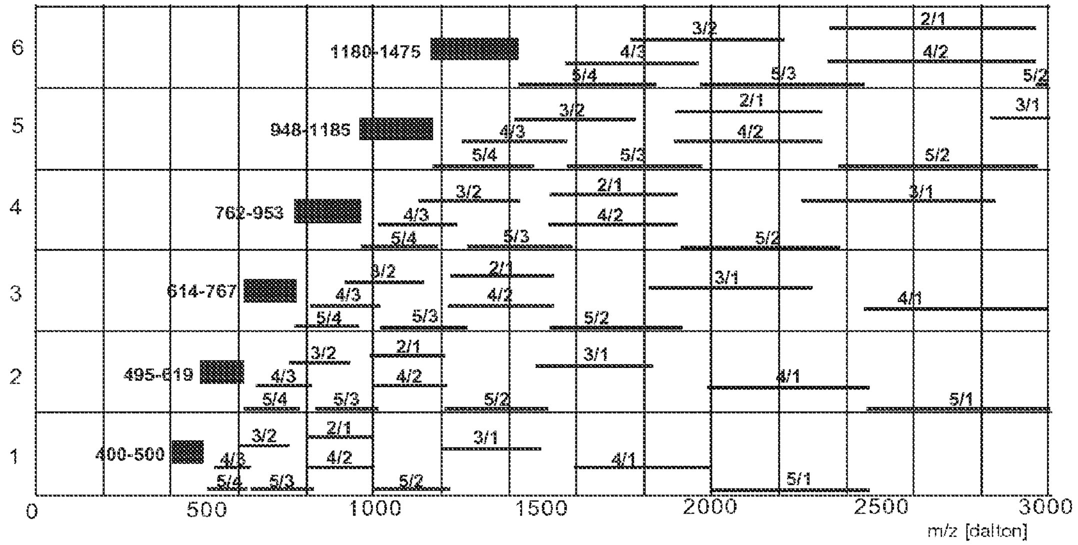
FIG. 3 depicts a diagram for six different measurement runs on the vertical axis vs. charge-related mass m/z on the horizontal axis, showing the isolation windows as black rectangles, and the m/z-ranges for different charge-reduced ions. The designation "4/3" means ions with originally z=4 charges, reduced to z=3 charges. The six measurement runs cover mass windows from m/z=400 up to m/z=1475 dalton; the windows are chosen such that the charge-reduced ions 5/4 appear completely outside the corresponding isolation window.

FIG. 3 depicts the charge reduction results of 6 different measurements in a single diagram, covering slightly overlapping isolation mass windows from m/z=400 up to m/z=1475 dalton. In each measurement 1 to 6, the isolation window is shown as a black rectangle; the horizontal lines represent the m/z-ranges for different charge-reduced ions. The designation "5/4" means ions with originally z=5 charges, reduced to z=4 charges. The isolation windows are chosen such that the charge-reduced ions 5/4 appear completely outside the corresponding isolation window. The diagram shows nicely how the charge-reduced ions distribute clearly over the range from the upper limit of the isolation mass window to the upper measurement limit of the mass spectrometer, here at m/z=3,000 dalton.

The charge reduction of positive digest peptide ions can be brought about in particular by proton transfer reactions (PTR) with non-radical anions of high proton affinity, but also by electron transfer reactions with special radical anions of low electron affinity. With electron transfer reactions the aim is usually to achieve fragmentation reactions by electron transfer dissociation (ETD), but if no special supporting measures for the dissociation are taken, this process produces mainly charge-reduced ions without dissociation; this process is often termed "ETnoD".

From the extraordinarily large number of background ions which are predominantly singly charged, the proton reduction reactions produce neutral particles. The charge stripping from singly charged ions is, however, relatively slow, so many of these singly charged background ions remain in this isolation mass range and have to be removed from the ion trap later together with all other ions remaining in the isolation mass window. Only the relatively rare multiply charged background ions can produce charge-reduced ions, which then appear in the mass spectrum which is subsequently acquired. These can easily be recognized as such because they do not show the characteristic structure of HPLC peaks, instead, they occur more or less continuously over the complete HPLC run. These ions can therefore be disregarded.

In order to measure all the charge-reduced ions from ions originally having up to four or five charges, the isolation mass window should be chosen to be only so wide in each case that it extends at most to a mass which is a factor of 1.33 or 1.25 respectively above the lowest mass $(m/z)_b$ of the isolation mass window. In FIG. 3, a factor of 1.25 was chosen; all charge-reduced ions outside this isolation mass window, including the transitions from quintuple charge to quadruple charge, can then be measured. If a lowest limit $(m/z)_b$=400 dalton is selected for the overall method, for example, the first isolation mass window should extend from m/z=400 to m/z=500 dalton. If the range from 400 to around 1400 dalton is selected as the desired total mass range, this results in only six isolation mass windows. Isolation mass windows with higher masses no longer make sense even in mass spectrometers which can measure up to a mass of 3,000 dalton, because many charge-reduced ions are then outside this acquisition range.

In order to achieve an advantageous filling, which in an RF ion trap means a maximum of 50,000 ions for a mass scan of good quality and optimum mass resolution, all the remaining ions of the isolation mass window are now ejected, for example simply by increasing the RF voltage so that the lower mass limit $(m/z)_{lim}$ for the ion storage is raised accordingly. The charge-reduced ions which are outside this isolation mass window can now be measured as a well-resolved mass spectrum. From this mass spectrum, which was acquired at the retention time t, the masses m, the charge states z and the intensities i of the ions of the digest peptides which are eluted at that time can be determined prior to the charge reduction. The complete method requires, with high overfilling, around 500 milliseconds for one mass range. It therefore takes only three seconds to repeat this method six times over the six isolation mass windows of the selection above, which will be called a "measurement cycle" here. The majority of peptides which are eluted at this retention time are therefore detected in this measurement cycle, provided that their mass-to-charge ratios m/z are in the selected total mass range between 400 and 1475 dalton.

This measurement cycle is now repeated continuously during the whole HPLC run so that it is carried out 3,600 times in three hours, and 21,600 mass spectra are acquired. This means that within each individual HPLC peak, which usually has a full width at half-maximum of around 10 to 15 seconds, several measurement cycles are performed. It is therefore possible to measure the data m, z, t and i for a high number of digest peptides of even a very complex proteome in a single HPLC run of three hours duration; most of the digest peptides found are far below the detection limit of usual mass spectra of the ions. Many measurements are automatically confirmed: the peptide ions of the different charge levels are to be seen across the HPLC peak of this peptide in three to five measurements; and ions of the same digest peptide are found with two or three different charge states z in the different mass ranges of the measurement cycle.

Figure 5:
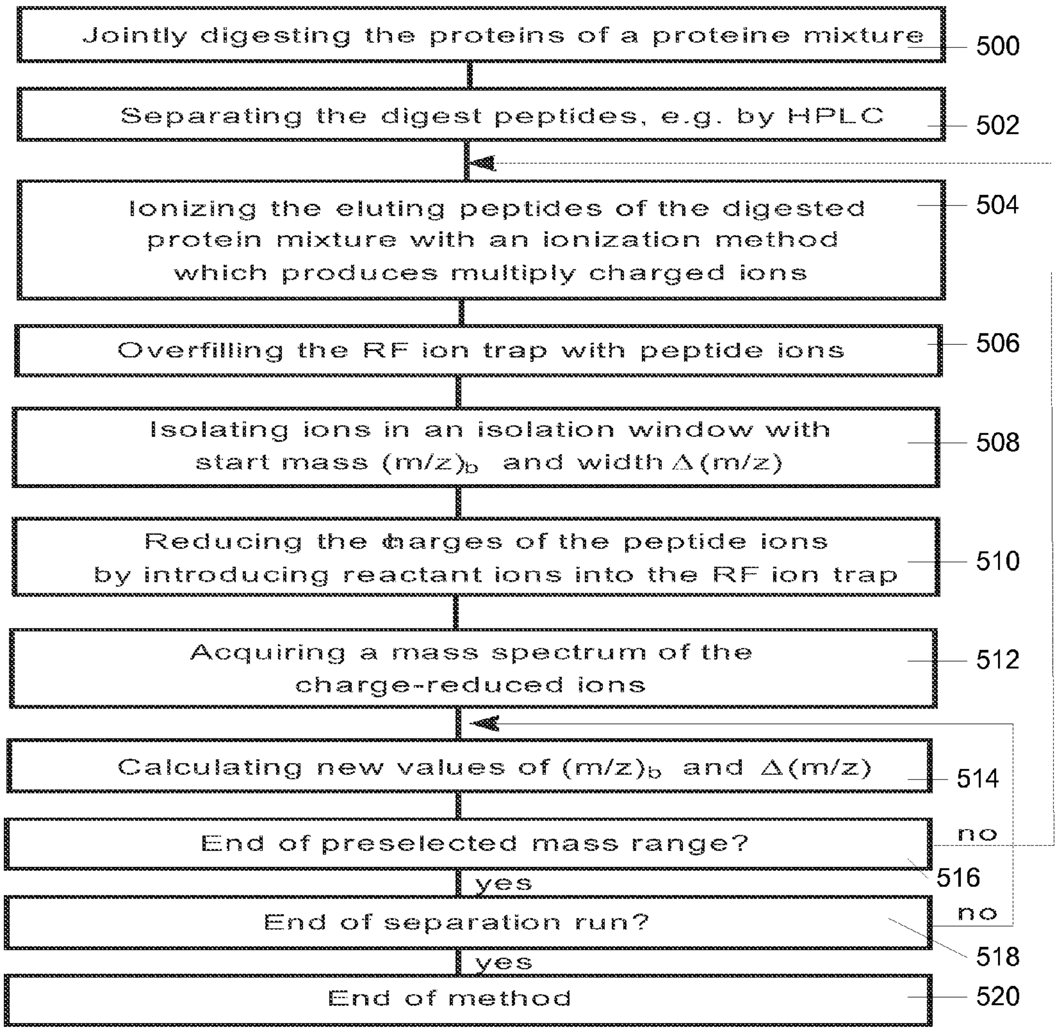
FIG. 5 is a flowchart of the steps of a simple embodiment of the method, using the RF ion trap for isolating and for the acquisition of the mass spectrum of the charge-reduced peptide ions.
Figure 6:
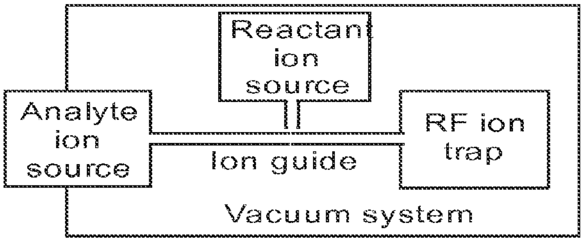
FIGS. 6 to 9 schematically depict different versions of mass spectrometers, with and without additive mass filters, and with and without separated ion analyzers with high mass resolution.
Figure 7:
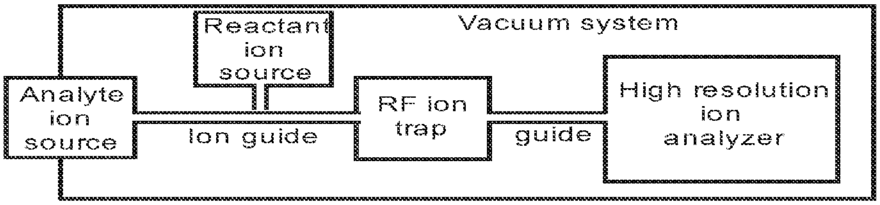

The method steps of a preferred embodiment are depicted in the flowchart of FIG. 5. This method begins in step 500 by jointly digesting the proteins of the protein mixture. The method proceeds to step 502 by separating the digest peptides by a separation method like HPLC or capillary electrophoresis. The method continues in step 504 by ionizing the peptides of the digested protein mixture with an ionization method which produces multiply charged ions. Next, step 506 comprises overfilling filling the RF ion trap with digest peptide ions. Step 508 follows by isolating ions in the trap having charge-related masses m/z within the initial isolation window between $(m/z)_b$ and $((m/z)_b+\Delta(m/z))$. Then step 510 comprises reducing the number z of charges of the peptide ions by introducing reactant ions into the RF ion trap. Step 512 follows by acquiring a mass spectrum of the charge-reduced ions. This process then proceeds to step 514 where a new isolation window is calculated. A check is made in step 516 to determine whether the heaviest mass $((m/z)_b+\Delta(m/z)$ in the newly-calculated isolation window exceeds the end of the preselected mass range. If not, the method proceeds back to step 504 and repeats steps 504-512 to acquire a new mass spectrum with the new isolation window.

Operation continues in this manner until the end of a newly-calculated isolation window reaches the end of the preselected mass range as determined in step 516. In that case, the method proceeds to step 518 to determine whether the end of the digest protein separation run has occurred. If not, then the method proceeds back to step 514 where a new isolation window is calculated using the parameters of the first or initial isolation window. The method then repeats steps 504-516 to acquire mass spectra over the selected mass range. This process is repeated until the end of the separation run is reached as determined in step 518. The method then finishes in step 520.

Figure 8:
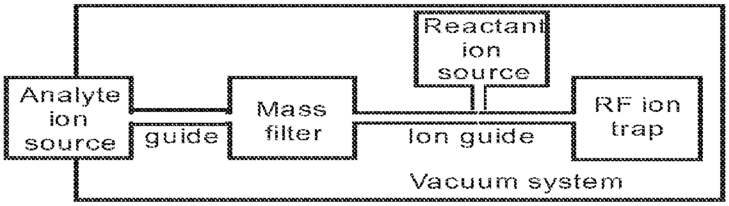
Figure 9:
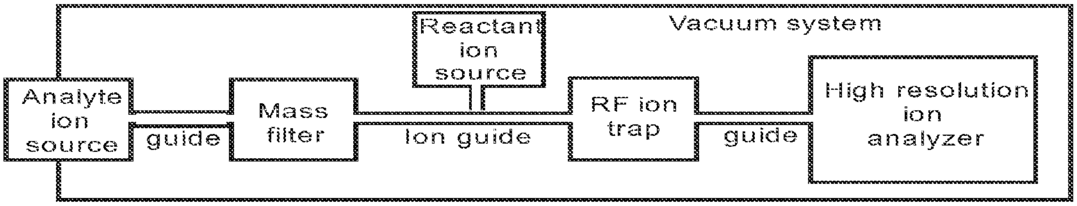
Figure 10:
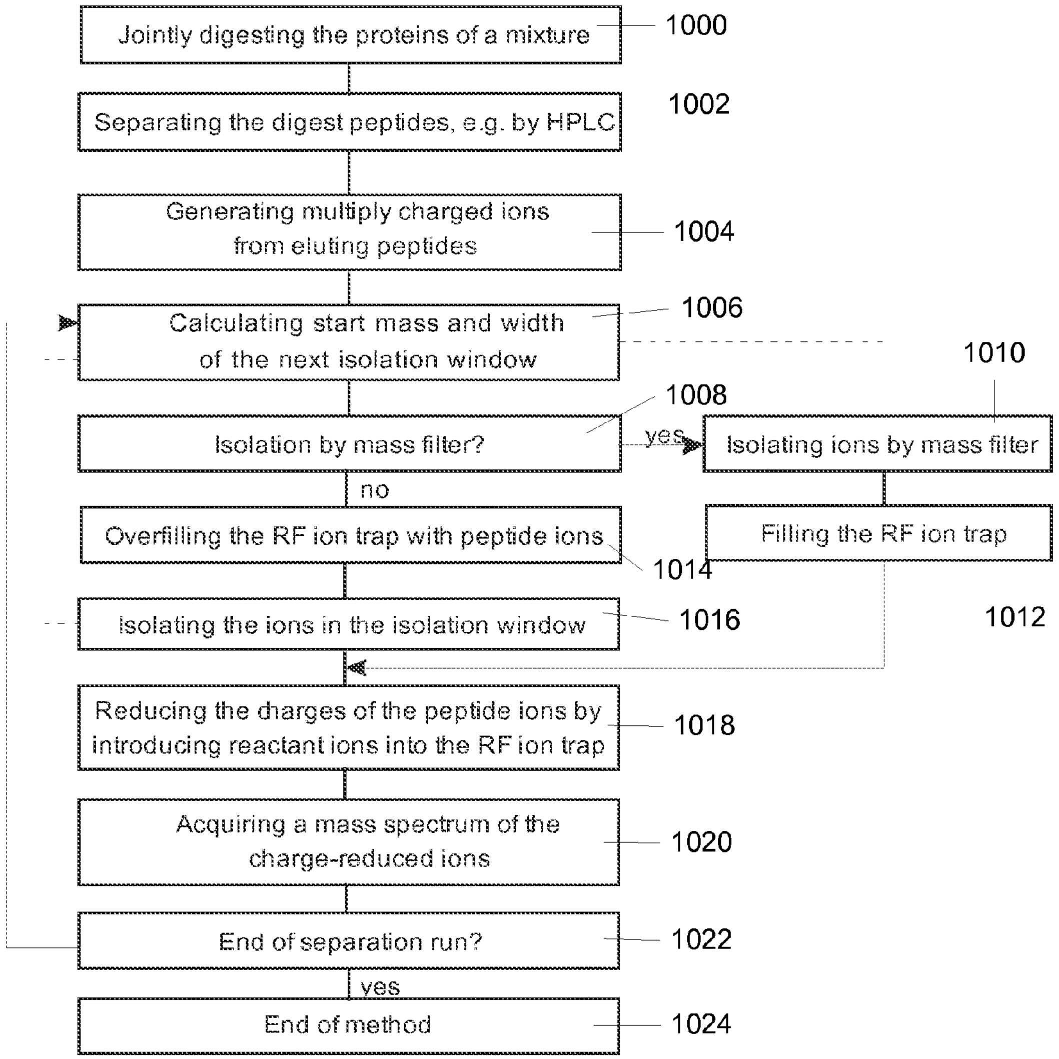
FIG. 10 is a flowchart showing the steps in a more complex method, allowing the filtering for the isolation of peptide ions either inside the ion trap, or by an upstream mass filter, as present in the mass spectrometers shown in FIGS. 8 and 9.

As an alternative, the RF ion trap can be filled with ions which are already filtered, for example, by an upstream mass filter, such as those present in mass spectrometers of the types shown in FIGS. 8 and 9. Here, also, the aim is to achieve a high overfill. The alternative use of a mass filter for ion isolation is presented in the block diagram of FIG. 10.

This alternative method begins in step 1000 by jointly digesting the proteins of the protein mixture. The method proceeds to step 1002 by separating the digest peptides by a separation method like HPLC or capillary electrophoresis.

The method continues in step 1004 by ionizing the peptides of the digested protein mixture with an ionization method which produces multiply charged ions. Next, step 1006 the start mass $(m/z)_b$ and width $\Delta(m/z)$ of the next (in this case first) isolation window are calculated.

In step 1008, a determination is made whether the ions will be isolated using a mass filter. If it is determined in step 1008 that a mass filter will be used, then the method proceeds to step 1010 where the mass filter is used to isolate the ions. Next, in step 1012, the RF ion trap is filled with the isolated ions.

Alternatively, if in step 1008 it is determined that a mass filter will not be used, then the method proceeds to step 1014 which comprises overfilling filling the RF ion trap with digest peptide ions. Step 1016 follows by isolating ions in the trap having charge-related masses m/z within the initial isolation window between $(m/z)_b$ and $((m/z)_b+\Delta(m/z))$.

In either case the method resumes at step 1018 which comprises reducing the number z of charges of the peptide ions by introducing reactant ions into the RF ion trap. Step 1020 follows by acquiring a mass spectrum of the charge-reduced ions. Next, the method proceeds to step 1022 to determine whether the end of the digest protein separation run has occurred. If not, then the method proceeds back to step 1006 where a new isolation window is calculated. The method then repeats steps 1006-1022 until the end of the separation run is reached as determined in step 1022. The method then finishes in step 1024.

In the method described, the mass spectrum of the charge-reduced ions is measured in the RF ion trap of the mass spectrometer itself. As has been mentioned above, however, this type of spectral acquisition has limited mass resolution and limited mass accuracy. It can therefore be much more advantageous to transfer the charge-reduced ions from the RF ion trap into another ion analyzer of higher mass resolution and mass accuracy, in mass spectrometers of the types shown in FIGS. 7 and 9, and to acquire the mass spectrum of the charge-reduced ions there. Various ion analyzers are suitable for this purpose: for example, time-of-flight ion analyzers with orthogonal ion injection (OTOF), ion cyclotron resonance ion analyzers (ICR) or electrostatic Kingdon ion trap analyzers.

The data m, z, t and i of the individual peptides can already provide information on the under-expression or over-expression of individual proteins when compared to reference measurements on other proteomes. This can already be used to detect stress states, such as tumorous or otherwise damaged tissue.

If desired, the knowledge of these data on the digest peptides also enables daughter ion spectra of the digest peptides to be acquired in only a few subsequent HPLC runs. The data m, z, t and i allow for the selection of ions of the most advantageous peptide mass m with the most advantageous charge state z as parent ions; these can be specifically collected at retention time t, isolated and fragmented in order to measure the daughter ion spectrum. In ion traps, the fragmentation is usually performed by collision-induced fragmentation; but it is also possible to carry out a fragmentation of the selected parent ions by electron transfer dissociation, for which the necessary radical anions can also be supplied by the electron attachment ion source (8) in FIG. 1. If, for example, the data of 50,000 digest peptides are determined in the first HPLC run, then the non-uniform distribution over time means that the daughter ion spectra of almost all the digest peptides can also be measured in a further two to four three-hour HPLC runs, in which it is possible to measure more than 30,000 daughter ion spectra each time, even if in some time windows a particularly large number of digest peptides are eluted. In a relatively short time of only a few hours, this method finds many times the number of proteins which can be found by methods used up to now.

The shorter duration of this method gives it the advantage over the PAcIFIC method of Panchaud et al. cited above, but it does not have the large dynamic range of measurement because, by necessity, it isolates all the ions from a much larger mass range. The dynamic range of measurement of the method according to the invention can be increased, however. To this end, a seventh, simple mass spectrum of the primary digest peptide ions is additionally acquired in each measurement cycle of originally six mass spectra of the different mass ranges, whereby all the digest peptides which are above the detection limit are found. All the particularly abundant peptide ions can be determined from this mass spectrum. The knowledge of these particularly abundant peptide ions allows the dynamic range of measurement in the isolation mass windows to be increased. This can be done by using resonant excitation for the targeted ejection of the digest peptide ions of outstanding abundance during each filling and isolation of the ions of an isolation mass window, which shifts the measurement range for the remaining digest peptide ions to lower concentrations. The resonant excitation can already take place during the filling. The particularly abundant peptide ions do not need to be completely removed; it is sufficient to reduce them to a few thousandths or hundredths of their original quantity. This allows the dynamic range of measurement to be increased by about two orders of magnitude. Further measures to increase the dynamic range of measurement are given below.

First, a detailed description will be given of an embodiment of the method which starts from a complex proteome in which around 50,000 digest peptides of the digestible proteins are expected, and which is designed in particular for the fast discovery of as yet unknown proteins.

Figure 4:
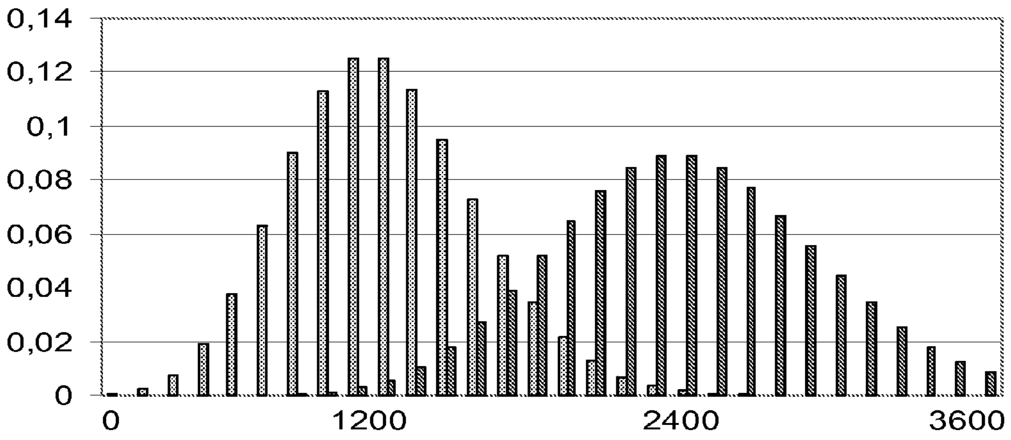
FIG. 4 shows two Poisson distributions representing the theoretical distributions of digest peptides resulting from two different enzymes. The left-hand Poisson distribution gives the theoretical distribution for a digest by trypsin, cutting the proteins after lysine and arginine, thus generating digest peptides with an average length of 10 amino acids. The resulting distribution shows a maximum at about 1200 dalton. In practice, however, for several reasons the digest delivers larger peptides, so that the true maximum of the distribution is shifted towards 1500 to 1600 dalton. The right-hand distribution is a theoretical distribution for an enzyme, which cuts only at one amino acid.

In this embodiment, the proteins of the proteome, for example the proteins of a cell community (e.g. a colony) of bacteria, are tryptically digested, producing several ten thousand digest peptides. If required, the digest is preceded by a disintegration of the cell walls, for example by using ultrasound. A "tryptic digestion" is a digestion by the enzyme trypsin, which cleaves the proteins specifically at each C-terminal of the two alkaline amino acids lysine and arginine if they are accessible. The resulting digest peptides have an average size of around ten to twelve amino acids (depending slightly on the statistical proportion of lysine and arginine in the proteome, and on steric and other obstructions of the digestion). The sizes vary in form of a Poisson distribution from one amino acid up to around 40 amino acids (the Poisson distributions for two averages of ten and twenty amino acids respectively are shown in FIG. 4; the distribution for an average of twenty amino acids may be obtained by an enzyme which cuts the amino acid chain at only one amino acid). The digest peptides cover the range from extreme hydrophilicity through to extreme hydrophobicity relatively uniformly.

The digest peptides of this proteome are now fed to a slow, high-resolution liquid chromatograph, with a flow rate of around ten to twenty microliters per minute, for example. A "reversed-phase" chromatograph is selected, which essentially separates according to hydrophobicity and hydrophilicity. This results in a relatively uniform separation of the digest peptides over time. Chromatography with ten to twenty microliters per minute is considered to be relatively easy to handle.

The eluate from the chromatographic column is introduced directly into an electrospray ion source. If a chromatography run lasts about three hours (approx. 11,000 seconds), and if the complete time for acquiring a mass spectrum of the charge-reduced ions is 500 milliseconds, then around 22,000 mass spectra can be recorded in total. The complete time of acquiring a mass spectrum with an ion trap mass spectrometer depends on the duration of the filling process, the duration of the isolation, the duration of the resonant ejection of the abundant peptide ions if required, the duration of the charge reduction and the duration of the concluding measurement of the mass spectrum of the charge-reduced peptide ions. Since the usual time for the acquisition of a daughter ion spectrum is only around 200 to 250 milliseconds, the time of 500 milliseconds here is on the high side and particularly takes into account the desired initial high overfilling of the ion trap in each case.

The method described in detail above for the scanning of the charge-reduced peptide ions in measurement cycles, each consisting of six spectrum acquisitions with isolation mass windows across the whole mass range of 400 to 1,475 dalton, can now be performed, with the possible inclusion of a seventh mass spectrum of the original ions which shows the abundant peptide ions, and with resonant ejection of these abundant peptide ions.

The charge reduction can preferably be performed by proton transfer reactions (PTR). To this end, negative reactant ions with high proton affinities are added, which steal a proton from the peptide ions when they come in close contact. FIG. 3 presents, in six diagrams, the resulting mass ranges for ions undergoing these charge-stripping reactions. The cross-sections for these reactions are high, because the ions attract one another. The cross-sections for identical peptide ions with different charge levels z are proportional to the square $z^2$ of the charge level z; quadruply charged ions have 16 times the cross-section of the singly charged ones, and four times the cross-section of the doubly charged ones. The deprotonation can therefore be controlled very simply by the duration of the interaction with the negative ions; the losses of singly charged ions can thus be kept relatively low, and the yield of deprotonation of originally triply, quadruply or quintuply charged ions is high. The negative reactant ions usually have charge-related masses m/z which are below the lower mass limit of the mass ranges set; for them to act, the RF voltage must be correspondingly decreased in order to introduce and store these ions. By later increasing the RF voltage, the negative reactant ions are immediately removed from the ion trap; the reaction is therefore abruptly stopped. As is described in the document U.S. Pat. No. 7,582,862 B2 (R. Hartmer, 2006) already cited above, suitable anions for the PTR can be generated from suitable substances in the electron attachment ion source of FIG. 2.

The charge reduction by PTR can also be stopped after the first deprotonation. This is done, in a way which is known as such, by subjecting the products of the charge reduction to a slight, resonant excitation by an applied excitation frequency. The permanent motion of the ions thus generated interrupts a further reaction by proton transfer, because only ions with relatively low relative velocity with respect to each other can react in this way. Thus, if a mixture of excitation frequencies for all ions outside the isolation mass window is applied during the charge reduction process, the charge reduction processes are largely stopped after the first stage. The mixture of excitation frequencies is applied at two opposing electrodes of the RF ion trap; in the case of a 3D ion trap, as shown in FIG. 1, usually at the two end cap electrodes.

The charge reduction can also be performed by electron transfer. The aim of electron transfer is generally to bring about a dissociation (ETD), but experience shows that a large number of multiply charged ions, especially in ion traps with largely stationary peptide ions, accept an electron but do not dissociate without further help. This reaction with ions which do not decompose is designated "ETnoD". The nature of ETnoD ions means they have a lower charge level; the masses m and charge levels z of the original peptide ions can also be calculated from them. At the same time, this reaction provides the dissociation products, i.e. the fragment ions for the daughter ion spectra.

The total mass range of 400 to 1,475 dalton, divided into six isolation windows, was selected arbitrarily above. The mass range can easily widened towards lighter masses m/z. It then includes quintuply charged ions of peptides with m/z<<2,000 dalton. These are produced only rarely in the electrospray ion source, however, and only a small amount of information can be obtained from such short peptides. For comparison: in the publication by Panchaud et al. cited above, a total mass range of 400 to 1,400 dalton was selected, and this mass range was chosen in the above example. If one wishes to also include the triply charged ions from peptides with eight amino acids (on average 900 dalton), and the quadruply charged ions from those with 10 amino acids (around 1,200 dalton), this would result in a lower limit of the total mass range of 300 dalton, but a correspondingly larger factor for the width of the isolation window may be used.

In the example given above and depicted in FIG. 3, a factor of 1.25 and an overlap of 5 dalton are assumed for demarcating the mass ranges from each other. This factor does not, however, take into account the fact that the isolation in greatly overfilled ion traps is only indistinctly delimited, so it may be better to select somewhat smaller and slightly more overlapping isolation mass windows. In order to leave space for the overlapping and the lack of sharpness in the isolation, it is better to select the factor for the determination of the upper mass range limits to be less than 1.25, for example only 1.125. The value of 1,400 dalton can favorably be chosen as the upper limit of the total mass range; all transitions from doubly to singly charged ions are then still within the mass range of the mass spectrometer, if it can measure in a mass range up to 3,000 dalton. With the factor 1.125, an overlapping of 10 dalton and a total mass range of 400 to 1,400 dalton, this results in 12 isolation mass windows for a measurement run, as shown in Table 1.

TABLE 1

Example with smaller isolation windows

| | | |
|---|---|---|
| 1 | 400 | 450 |
| 2 | 440 | 495 |
| 3 | 485 | 546 |
| 4 | 536 | 603 |
| 5 | 593 | 667 |
| 6 | 657 | 739 |
| 7 | 729 | 820 |
| 8 | 810 | 911 |
| 9 | 901 | 1014 |
| 10 | 1004 | 1129 |
| 11 | 1119 | 1259 |
| 12 | 1249 | 1405 |

With such longer measurement runs over 12 isolation windows, it is still possible to acquire each spectrum twice inside the chromatographic peak during the measurement run, and using the results to remove not only the highly abundant ions but also the less abundant ions, which were only discovered in the first spectrum, in the second scan. This makes it possible to again increase the dynamic range of measurement.

This single or also double measurement run of the method is now continuously repeated during the whole HPLC run so that the just over 22,000 mass spectra with charge-reduced peptide ions are acquired within three hours' operating time. As anyone skilled in the art knows, the charge level of any peptide ion can be derived from the width of the isotopic pattern on the mass scale. Each individual HPLC peak of each peptide, which usually has a full width at half-maximum of around 10 to 15 seconds, is therefore scanned several times in all isolation mass windows. As was described above in detail, it is thus possible to obtain the data m, z, t and i for almost all the digest peptides of a proteome in a single HPLC run of three hours' duration from the mass spectra; most of the digest peptides found are far below the detection limit of the usual ion spectra. Many mutual confirmations are automatically contained in these mass spectra, on the one hand because the peptide ions of the different charge levels are followed across the HPLC peak of this peptide in several measurements and, on the other hand, because ions of the same peptide are found with two or three different charge states z in the different mass ranges.

It is also possible to split these measurements into two or more successive HPLC runs, of course. Such a split can be done in different ways; it is left to those skilled in the art to carry out this split to suit the objective. Such splits can particularly be used to further increase the dynamic range of measurement.

As has already been described above, the data m, z, t and i for the ions of the individual digest peptides are in themselves very valuable because, by comparing with reference measurements on reference proteomes, it is possible to determine over-expressions and under-expressions of individual proteins, particularly of proteins in the lower concentration range.

With these data it is also possible to acquire the daughter ion spectra of many peptide ions in subsequent HPLC runs; and now it is no longer necessary to search "blindly" (or "data independent"), but instead the search can be quite "specific" (or "data dependent"). It is advantageous here to use the data to first develop a strategy regarding at which retention time, which peptide with which charge state is the best way to acquire a daughter ion spectrum. Since in some retention time windows the peptides are closer together than in others, and only around three to four daughter ion spectra per second can be acquired in one HPLC run, the measurements must be divided between two HPLC runs, or even three in more unfavorable cases. Computer programs may help in planning this strategy.

Daughter ion spectra may be acquired in a known way with fragmentation performed by ion collisions with molecules of the damping gas (CID, collisionally induced decomposition), but also with electron transfer dissociation (ETD), where the special radical anions required for these reactions can also be generated in the electron attachment ion source of FIG. 2. For the acquisition of these daughter ion spectra, it is advantageous to leave no ETnoD ions in the ion trap; it is a common technique to force these ions which do not decompose to undergo collisions by slight resonance excitation, which causes them to decompose into the desired daughter ions.

After the daughter ion spectra have been acquired, a protein search in a reference protein sequence database is started, using one of several well-known search engines. The search engine is a program which conducts an intelligent search in the database for the protein which contains this digest peptide. Usually, this search is unequivocal because the daughter ion spectra of the digest peptides are very specific to the proteins, particularly if they are longer digest peptides. It is also immediately recognizable whether the protein belonging to the peptide is in the database or not. The search, normally carried out on a server reserved for the task, is very quick; it usually only takes around one second per daughter ion spectrum.

As an example, the continuously updated database "SwissProt™" (Geneva Bioinformatics S.A., Geneva), can be used as the protein sequence library for the known proteins, for example. But other databases can also be used here, for example the NCBInr database from the National Institute of Health, USA, which contains not only protein data but also genome data. One search engine to mention is the Mascot™ program from Matrix Science Ltd., London, for example, but here again there are several comparable search engines on the market. The search can be performed via the Internet, for more data safety also in-house (via intranet) if the database (by appropriate contracts) and the weekly updates of the database are downloaded from the Internet onto in-house servers.

If a protein belonging to a peptide is found, this protein is listed and marked as temporarily identified (but without any confirmation as yet). Depending on the analytical objective assumed here, the protein may or may not be of further interest for the subsequent analysis. The structure of this protein can be downloaded from the database and "virtually" digested by a program. With this information the precise masses of all the other digest peptides can be calculated. In addition, the hydrophobicity of these virtual digest peptides can be determined using their amino acid composition and their sequence. The retention time of this peptide for the "reversed phase" chromatography used can be determined reasonably well from the hydrophobicity. In the relevant retention time window, all the masses of the real digest peptides can now be compared with the mass of the virtual digest peptide in order to ascertain the presence of this protein. If such a peptide is found, its daughter ion spectrum can serve as a further confirmation. The number of peptides found belonging to the protein may already constitute a confirmation for a correct identification, but for further confirmation, the other daughter ion spectra can also be measured.

In this way, after the second HPLC run (the first one with measurements of daughter ion spectra), the certain identification of a large number of proteins can already modify the further measurement strategy for the third run in order to avoid having to measure fourth or fifth daughter ion spectra of digest peptides involved for definitely identified proteins.

All of the peptides which are not belonging to known proteins of the database belong to unknown proteins. These must finally be subjected to a search in a cDNA or DNA database to identify them and determine their belonging to a protein. The EST databases (Expressed Sequence Tags) are available as cDNA databases, although they usually do not contain the complete sequence of the protein. Complete cDNA databases are being set up, however. The genome databases usually available in the Internet can be used as DNA databases, and are now reasonably complete for many species (including humans).

This procedure is preferred only when the main objective is the identification of previously unknown proteins of a proteome. Since there are many objectives for proteome analyses, the measurement strategy used can be quite different for other objectives. For example, the objective can be to not only identify as many proteins of a proteome as possible, but also to determine their posttranslational modifications (PTM).

For the identification of posttranslational modifications, it is particularly advantageous to carry out both fragmentation methods, CID and ETD, for all digest peptide ions, as far as possible, in the further HPLC runs. With collision-induced fragmentation (CID), all side chains such as phosphorylations or glycosylations from posttranslational modifications (PTM) are lost; with electron transfer dissociation (ETD), they are retained. The comparison thus provides the identification of the posttranslational modifications of the proteins in the ranges of the digest peptides measured. For this objective, it can therefore also be advantageous to include very small digest peptides because they can also be posttranslationally modified.

It is also possible to follow other, completely different objectives with the method according to the invention, each of which aims to also find those digest peptides which are normally below the detection limit. A very elegant embodiment of the method according to the invention, which will be briefly explained here, relates to an analytical task whose aim is to achieve a more accurate quantification of the expression of proteins than is possible via the determination of the intensities i. Particularly interesting is the analysis of the differences in the expression of proteins in two differently stressed cell communities. This analysis can be used to detect reactions of the cells to external or internal stress conditions and to obtain an insight into the behavior and operation of cells.

For these investigations, it is again expedient to analyze whole proteomes. The first step is therefore to digest the proteomes of normal and stressed cell communities. The dissolved proteins of the two proteomes are now modified by markers before the mixing in such a way that the markers can be differentiated mass spectrometrically and that the association of a protein with one proteome or the other remains recognizable. The mixture of the two proteomes with the marked proteins is then enzymatically digested jointly.

A particularly advantageous marking method has become known by the acronym "ICAT", which stands for "isotopically coded affinity tag". An ICAT reagent for the marking modification comprises a reactive group which can react with a specific amino acid, for example with the thiol group of cystine; it further comprises an affinity group, for example biotin, which can be used for an affinity extraction (here, for example, with streptavidine), and a linker in two different isotope-marked forms. This not only involves a modification which can be differentiated by mass spectrometry, but one which also contains a very specific affinity group, so that it is possible to extract the modified proteins or, after the joint digestion, the modified digest peptides and to separate them from the unmodified proteins or digest peptides. Biotin is used as the affinity group, for example; this biotin is bonded by the linker and a reaction group to a cystine, for example. The linker contains eight hydrogen atoms which are bonded so tightly that they cannot exchange in solution. The isotopic coding now consists in the linker in one case containing eight normal hydrogen atoms, in the other case eight deuterium atoms. Thus the two modifications differ by eight dalton.

The marked digest peptides are now subjected to affinity extraction. The extraction is performed using, for example, small magnetic beads, whose surface is coated with streptavidin and which bind the biotin groups by affinity. After washing, the marked digest peptides can be detached again from the streptavidin by careful addition of ammonia. The marked digest peptides are now separated by means of liquid chromatography, as in the method described above, and introduced to the special analytical method in the ion trap mass spectrometer.

Since the isotopic marking of the modifications practically does not result in different retention times, the differently coded, corresponding digest peptides from both proteomes become visible next to each other in the mass spectra of the charge-reduced, marked digest peptides. If the two proteins are equally expressed, the digest peptide spectrum contains two isotopic groups of equal intensity which differ by eight dalton (or with two cystines in the digest peptide, by 16 dalton). The groups of the same intensity are not interesting according to the objective of the analysis; the interesting ones are those groups where the intensities are different. Sometimes only one group appears; this can then be a protein which is generated only in the stress situation, or is no longer generated at all in the stress situation. The difference (or ratio) in the intensities can be used to select those peptides whose daughter ion spectra need to be measured. The daughter ion spectra can in turn be used to identify the proteins which are subject to a different expression. This method can also be carried out with more than two proteomes, where the markings should represent the association with one of the proteomes.

Several preferred embodiments of the invention have been described in detail here for various analytical objectives. In addition, there are a large number of adaptations for the fundamental method which depend on the analytical objective. The knowledge of this invention enables those skilled in the art to carry out adaptations of the method to suit their analytical objective.

While the invention has been shown and described with reference to a number of embodiments thereof, it will be recognized by those skilled in the art that various changes in form and detail may be made herein without departing from the spirit and scope of the invention as defined by the appended claims.

What is claimed is:

1. A method for the mass spectrometric analysis of a protein mixture in a mass spectrometer containing an RF ion trap, comprising:

(a) digesting proteins of the protein mixture to form digest peptides;

(b) separating the digest peptides by one of a chromatographic and electrophoretic process to elute digest peptides;

(c) ionizing the eluting digest peptides with an ionization method producing multiply charged ions;

(d) filling the RF ion trap with digest peptide ions having masses between a start mass $(m/z)_b$ and an end mass $((m/z)_b+\Delta(m/z))$ forming a mass window;

(e) reducing the charge of the peptide ions by introducing reactant ions into the RF ion trap wherein the m/z values of the charge-reduced peptide ions are shifted out of the mass window;

(f) separating the ions with m/z values remaining in the mass window from those ions whose m/z values lie outside the window; and (g) acquiring a mass spectrum of the charge-reduced peptide ions.

2. The method of claim 1, wherein step (d) comprises using an isolation process within the RF ion trap to fill the RF ion trap with digest peptide ions having masses between a start mass $(m/z)_b$ and an end mass $((m/z)_b+\Delta(m/z))$.

3. The method of claim 1, wherein step (d) comprises mass filtering the digest peptide ions before the digest peptide ions are filled into the ion trap in order to fill the RF ion trap with peptide ions having masses between a start mass $(m/z)_b$ and an end mass $((m/z)_b+\Delta(m/z))$.

4. The method of claim 1, wherein step (e) comprises reducing the charge of the digest peptide ions by one of proton transfer and electron transfer reactions.

5. The method of claim 4, wherein step (e) comprises reducing the charge of the digest peptide ions by proton transfer reactions and stopping the proton transfer reactions after a first charge reduction stage by resonant excitation of charge-reduced ions.

6. The method of claim 1 wherein step (b) comprises:

(b1) repeating steps (c) to (g) a plurality of times, each time increasing $(m/z)_b$ and $\Delta(m/z)$ so that a predetermined total mass range is covered.

7. The method of claim 6 wherein step (b) further comprises:

(b2) resetting $(m/z)_b$ and $\Delta(m/z)$ to an initial value; and (b3) repeating steps (b1) and (b2) until the one process in step (b) is completed.

8. The method of claim 7, further comprising determining masses m, original charge numbers z before charge reduction, intensities i, and retention times t of the digest peptides from mass spectra acquired in step (g) during each repetition in step (b3).

9. The method of claim 8, wherein during at least one repetition in step (b3), digest peptides with preselected masses m, charge numbers z and retention times t are isolated and fragmented, and daughter ion spectra are acquired of the selected peptides.

10. The method of claim 9, wherein the daughter ion spectra are acquired with fragmentation of the digest peptide ions by collisions with molecules of a damping gas (CID) in the RF ion trap.

11. The method of claim 9, wherein the daughter ion spectra are acquired with fragmentation of the digest peptide ions by electron transfer dissociation (ETD).

12. The method of claim 9, wherein proteins belonging to the digest peptides, are identified from the daughter ion spectra of the digest peptides by searches in at least one of protein sequence, cDNA and DNA databases.

13. The method of claim 1, wherein the protein mixture is a proteome.

14. The method of claim 1, wherein the protein mixture is a mixture of proteins from at least two proteomes and wherein a proteome to which at least some of the proteins belong is identified by making modifications of the at least some proteins which modifications can be distinguished by different masses.

15. The method of claim 1, wherein step (g) comprises acquiring the mass spectrum of the charge-reduced ions with the RF ion trap used as ion analyzer.

16. The method of claim 1, wherein step (g) further comprises transferring the charge-reduced ions from the RF ion trap to a separate ion analyzer, and acquiring the mass spectrum of the charge-reduced ions by the separate ion analyzer.

17. The method of claim 16, wherein the separate ion analyzer comprises one of a time-of-flight mass spectrometer, an ion cyclotron resonance mass spectrometer and a Kingdon trap mass spectrometer.

18. The method of claim 1, wherein step (c) comprises ionizing the eluting digest peptides with electrospray ionization.

19. The method of claim 1, wherein in step (d) an RF voltage of the RF ion trap is set so that the start mass $(m/z)_b$ of the mass window coincides with a lower cut-off mass $(m/z)_{lim}$ for ion storage in the ion trap.

20. The method of claim 6, wherein, after the predetermined total mass range has been covered, another mass spectrum of primary digest peptide ions is acquired from which all the primary digest peptides that are above the detection limit are determined.

* * * * *